(12) United States Patent
Riermeier et al.

(10) Patent No.: US 6,566,571 B1
(45) Date of Patent: May 20, 2003

(54) METHOD OF PRODUCING BIARYLS

(75) Inventors: Thomas Riermeier, Floersheim (DE); Matthias Beller, Rostock (DE); Alexander Zapf, Rosenheim (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/926,269

(22) PCT Filed: Feb. 11, 2000

(86) PCT No.: PCT/EP00/01111

§ 371 (c)(1),
(2), (4) Date: Feb. 4, 2002

(87) PCT Pub. No.: WO00/61531

PCT Pub. Date: Oct. 19, 2000

(30) Foreign Application Priority Data

Apr. 10, 1999 (DE) .......................... 199 16 222

(51) Int. Cl.$^7$ .......................... C07C 15/067; C07C 2/58
(52) U.S. Cl. .................. 585/446; 585/455; 585/457; 568/628; 549/412; 562/93; 564/409
(58) Field of Search ................. 538/446, 455, 538/457, 466; 568/628; 549/412; 562/93; 564/409

(56) References Cited

U.S. PATENT DOCUMENTS 5,254,776 A    10/1993   Lang et al. .................. 570/190

FOREIGN PATENT DOCUMENTS

| DE | 3925437 | 9/1990 |
| DE | 4414499 | 11/1995 |
| EP | 0501268 | 9/1992 |
| WO | 93/10106 | 5/1993 |

OTHER PUBLICATIONS

J.P. Wolfe, et al.: A highly active catalyst for the room–temperature animation and Suzuki coupling of arylchlorides Chemical Abstracts, 38(16), pp. 2413–2416 1999.

*Primary Examiner*—Thuan D. Dang
(74) *Attorney, Agent, or Firm*—Oblon, Spivak, McClelland, Maier & Neustadt, P.C.

(57) ABSTRACT

Process for preparing monofunctional, bifunctional and/or polyfunctional biaryls of the formula (I)

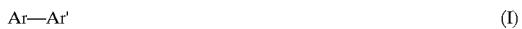

(I)

by reacting haloaromatics of the formula (II)

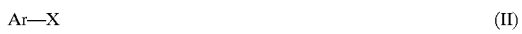

(II)

with boron compounds of the formula (IIIa), (IIIb) and/or (IIIc)

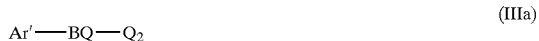

(IIIa)

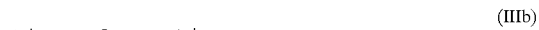

(IIIb)

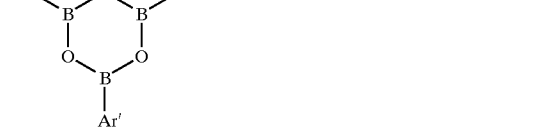

(IIIc)

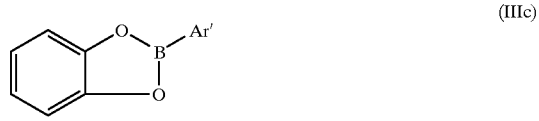

in the presence of at least one palladium complex of the formula (IVa) or (IVb)

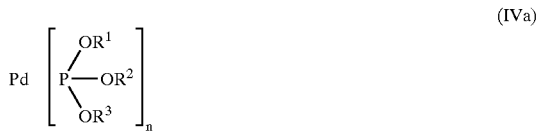

(IVa)

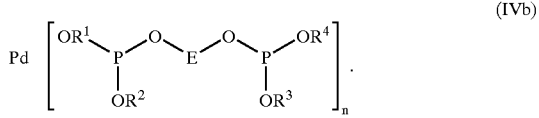

(IVb)

35 Claims, No Drawings

METHOD OF PRODUCING BIARYLS

DESCRIPTION

The present invention relates to a process for preparing biaryls using catalysts based on palladium compounds with phosphite ligands.

Biaryl compounds, in particular biphenyl compounds, are industrially important as fine chemicals, intermediates for pharmaceuticals, optical brighteners and agro-chemicals.

A method which is frequently employed for the synthesis of biaryls on a laboratory scale is the Suzuki reaction in which iodoaromatics or bromoaromatics or in exceptional cases chloroaromatics are reacted with arylboronic, vinylboronic or alkylboronic acid derivatives in the presence of palladium catalysts. Review articles describing this methodology may be found, for example, in N. Miyaura, A. Suzuki, Chem. Rev. 1995, 95, 2457. Catalysts used for the purposes of the Suzuki reaction are in general palladium and nickel compounds. Despite the economic advantage of nickel catalysts (cf. A. F. Indolese, Tetrahedron Lett. 1997, 38, 3513), palladium catalysts are preferred to nickel catalysts because of the lower toxicity and the greater tolerance to functional groups. When using palladium catalysts, both palladium(II) and palladium(0) complexes are employed in Suzuki reactions (cf. M. Beller, H. Fischer, W. A. Herrmann, K. Öfele, C. Broβmer, Angew. Chem. 1995, 107, 1992). According to the literature, coordinatively unsaturated 14- and 16-electron palladium(0) species stabilized by means of donor ligands such as phosphines are formulated as catalytically active species. Particularly when using relatively low-cost starting materials such as aryl bromides or aryl chlorides, it is necessary to add stabilizing ligands in order to achieve a satisfactory catalytic activation of the starting materials.

A substantial disadvantage of the Suzuki reactions described is that satisfactory catalytic turnover numbers (TONs) can be achieved only when using uneconomical starting materials such as iodoaromatics and activated (i.e. electron-deficient) bromoaromatics. Otherwise, when using deactivated (i.e. electron-rich) bromoaromatics or chloroaromatics, large amounts of catalysts, usually from 1 to 5 mol %, have to be added so as to achieve industrially usable conversions. Owing to the complexity of the reaction mixtures, simple catalyst recycling is also not possible, so that catalyst costs, too, generally stand in the way of industrial implementation. Relatively recent catalyst systems based on water-soluble phosphines do give satisfactory catalytic activities in the industrially important reaction of 2-chlorobenzonitrile with p-tolylboronic acid, but the catalysts comprise relatively expensive sulfonated phosphines. Furthermore, a number of chloroaromatics cannot be activated in an industrially satisfactory manner even by means of these catalysts (cf. S. Haber, Fine Chemical Syntheses, in B. Cornils, W. A. Herrmann, Aqueous Phase Organometallic Catalysis, Wiley-VCH: Weinheim, N.Y., Chichester 1998, p. 440 ff.).

It is an object of the present invention to provide a novel process for preparing biaryls which does not display the disadvantages of the known processes, is suitable for industrial implementation and gives biaryls in high yield, catalyst productivity and purity.

This object is achieved by a process for preparing monofunctional, bifunctional and/or polyfunctional biaryls of the formula (I)

$$Ar\text{—}Ar' \quad (I)$$

where Ar and Ar' are each, independently of one another,
an aromatic radical having up to 14 carbon atoms or
a heteroaromatic selected from the group consisting of five-, six- or seven-membered rings having at least one nitrogen, oxygen and/or sulfur atom in the ring;

by reacting haloaromatics of the formula (II)

$$Ar\text{—}X \quad (II)$$

with boron compounds of the formula (IIIa), (IIIb) and/or (IIIc)

(IIIa)

(IIIb)

(IIIc)

where, in the formulae (II), (IIIa), (IIIb) and (IIIc),

Ar and Ar' are as defined for formula (I);

X is selected from the group consisting of chlorine, bromine, iodine, $OSO_2CF_3$, $OSO_2aryl\text{-}(C_6\text{–}C_{10})$, $OSO_2alkyl\text{-}(C_1\text{–}C_8)$ and $N_2^+Y^-$, where Y is a chlorine, bromine or iodine atom or a tetrafluoro-borate or tetraphenylborate anion;

$Q_1$ and $Q_2$ are selected independently from the group consisting of OH, fluorine, chlorine, bromine, iodine, alkyl-$(C_1\text{–}C_4)$, aryl-$(C_6\text{–}C_{10})$, alkoxy-$(C_1\text{–}C_4)$ and aryloxy-$(C_6\text{–}C_{10})$;

in the presence of at least one palladium complex of the formula (IVa) or (IVb),

(IVa)

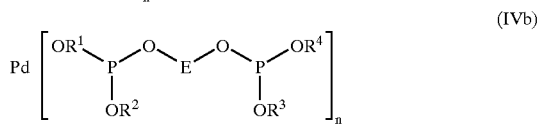
(IVb)

where the radicals $R^1$ to $R^4$ are each, independently of one another, a $(C_1\text{–}C_{18})$-alkyl radical or one of the above-described radicals Ar;

E is a carbon bridge having from two to seven carbon atoms; and n is an integer from 1 to 4.

In a further embodiment of the invention, the aromatic radicals Ar and Ar' have up to eight substituents;

the heteroaromatic has up to five substituents; and/or the radicals $R^1$ to $R^4$ have up to eight substituents which are selected independently from the group consisting of fluorine, chlorine, $CF_3$, OH, $NO_2$, CN, $R^5$, O—$R^5$, CHO, CO—$R^5$, COOH, COO—$R^5$, OCO—$R^5$, $SiR^5_3$, $NH_2$, $NH-R^5$, $N-R^5{}_2$, $SO-R^5$, $SO_2-R^5$, $SO_3H$, $SO_3-R^5$, $CONH_2$, $NHCOH$, $NHCO-R^5$, $NHCOO-R^5$, $CHCH-CO_2$-alkyl-$(C_1-C_8)$, $PO-R^5{}_2$, $P-R^5{}_2$, $PO_3H_2$, $PO(O$-alkyl-$(C_1-C_6))_2$ and $CHCHCO_2H$; where $R^5$ is an alkyl radical having from 1 to 8 carbon atoms or an aryl radical having from 6 to 10 carbon atoms, e.g. phenyl.

In the formula (IVb), the carbon bridge E can have up to seven substituents selected independently from the group consisting of $(C_1-C_4)$-alkyl, O-alkyl-$(C_1-C_4)$, OH and Ar, where Ar is as defined for formula (I).

It is likewise possible for $Q_1$ and $Q_2$ in the formula (IIIa) each to be, independently of one another, a $(C_1-C_4)$-alkyl, $(C_1-C_4)$-alkoxy, $(C_6-C_{10})$-aryl or $(C_6-C_{10})$-aryloxy radical which is substituted by at least one halogen atom or a $(C_1-C_4)$-alkoxy or $(C_1-C_4)$-alkyl radical; or for $Q_1$ and $Q_2$ in the formula (IIIa) together to form an alkylenedioxy or alkylene group which has from one to four carbon atoms and may be substituted by up to four $(C_1-C_4)$-alkyl and/or $(C_6-C_{10})$-aryl radicals.

The radicals Ar and Ar' can each be, independently of one another, a heteroaromatic in which up to four further aromatic, heteroaromatic and/or aliphatic rings are fused onto the heteroaromatic ring. The process of the invention is particularly suitable for the synthesis of biaryls in which Ar and Ar' are each a substituted phenyl, naphthyl, anthryl, phenanthryl, biphenyl radical and/or a five-, six- or seven-membered heteroaromatic having nitrogen, oxygen or sulfur atoms in the ring. In the case of hetero-aromatics, particular preference is given to hetero-aromatics such as substituted pyridines, pyrimidines, oxazoles, imidazoles, pyrazines, quinolines, indoles, furans, benzofurans and/or thiophenes.

The process of the invention has been found to be particularly useful for preparing compounds of the formula (I) in which the radicals Ar and Ar' each have, independently of one another, up to 5 substituents selected from the group consisting of alkyl-$(C_1-C_8)$, O-alkyl-$(C_1-C_8)$, OCO-alkyl-$(C_1-C_8)$, N-alkyl$_2$-$(C_1-C_8)$, phenyl, aryl, fluorine, chlorine, $NO_2$, CN, COOH, CHO, $SO_2$-alkyl-$(C_1-C_4)$, NH-alkyl-$(C_1-C_8)$, COO-alkyl-$(C_1-C_8)$, $CONH_2$, CONH-alkyl-$(C_1-C_8)$, CO-alkyl-$(C_1-C_8)$, CO-phenyl and PO-phenyl$_2$.

The reaction generally takes place in the presence of at least one solvent selected from the group consisting of water, aliphatic ethers, aromatic or aliphatic hydrocarbons, alcohols, esters, aromatic or aliphatic nitriles and dipolar aprotic solvents such as dialkyl sulfoxides, N,N-dialkylamides of aliphatic carboxylic acids or alkylated lactams. The solvent is preferably THF, dioxane, diethyl ether, diglyme, MTBE, DME, acetonitrile, toluene, xylenes, anisole, ethyl acetate, methanol, ethanol, butanol, ethylene glycol, ethylene carbonate, propylene carbonate, dimethyl sulfoxide, N,N-dimethylacetamide, N,N-dimethylformamide or N-methylpyrrolidone.

Since an acid is formed in the reaction, it is advantageous to neutralize the resulting acid by addition of a base. Bases suitable for this purpose are:

primary, secondary and tertiary amines such as alkylamines, dialkylamines, trialkylamines, each of which may be alicyclic or open-chain;

alkali metal and alkaline earth metal salts of aliphatic or/and aromatic carboxylic acids, e.g. acetates, propionates, benzoates, in particular their carbonates, hydrogen-carbonates, phosphates, hydrogenphosphates or/and hydroxides; and metal alkoxides, in particular alkali metal or alkaline earth metal alkoxides, e.g. sodium methoxide, potassium methoxide, sodium ethoxide, magnesium methoxide and calcium ethoxide.

The base is most preferably a carbonate, hydroxide or phosphate of lithium, sodium, potassium, calcium, magnesium or cesium.

Apart from neutralization of the acid formed, the base used can also have a positive influence on the course of the reaction by activating the arylboronic acid to form anionic boranate species. Apart from use of the abovementioned bases, such activation can also be achieved by addition of fluoride salts such as $CaF_2$, NaF, KF, LiF, CsF or $(C_1-C_8)$-alkyl$_4$NF.

The palladium catalysts of the formula (IVa) or (IVb) which are used are generally produced in situ from at least one palladium(II) salt or a palladium(0) compound and the corresponding phosphite ligands. However, they can also be used directly as palladium(0) compound without the initial catalytic activity being reduced thereby. The palladium(II) salt is preferably selected from the group consisting of palladium(II) acetate, palladium(II) chloride, palladium(II) bromide, lithium tetrachloropalladate(II), palladium(II) acetylacetonate, palladium(II) propionate, bis(acetonitrile) palladium(II) chloride, bis(triphenylphosphine)palladium (II) dichloride and bis(benzonitrile)palladium(II) chloride. The palladium(0) compound is, in particular, selected from the group consisting of palladium(0) dibenzylideneacetone complexes, tetrakis(triphenyl phosphite)palladium(0), tetrakis(triethyl phosphite)-palladium(0), tetrakis (triphenylphosphine)palladium(0), bis(tri-o-tolylphosphine) palladium(0), tricyclohexyl-phosphinepalladium(0) diallyl ether complex and bis(tricyclohexylphosphine)palladium (0).

The molar ratio of palladium to phosphite ligand should be less than 1 and is preferably in the range from 1:2 to 1:1 000, in particular from 1:5 to 1:200.

When using chloroaromatics, bromoaromatics, aryl triflates and/or aryl mesylates or related starting materials, it may be advantageous to use a cocatalyst in addition to the palladium-phosphite catalyst. This cocatalyst is selected from the group consisting of halogen salts, in particular a halide of the alkali metals and/or alkaline earth metals, an ammonium halide and/or a phosphonium halide, preferably a bromide or/and chloride. Particularly preferred halogen salts are LiBr, LiCl, NaBr, KBr, CsBr, Bu$_4$NCl, Bu$_4$NBr, benzyltrimethylammonium bromide, trioctylmethylammonium bromide or tetraphenylphosphonium bromide. The cocatalyst is usually used in an amount of from 0.001 mol % to 100 mol %, in particular from 0.01 to 50 mol %, based on the compound of the formula (II). If there are process engineering advantages, the reaction can also be carried out in the cocatalyst as solvent (salt melt).

The reaction is generally carried out at a temperature of from 20 to 200° C., preferably from 60 to 180° C., in particular from 80 to 160° C., and at a pressure of up to 100 bar, preferably at a pressure in the range from atmospheric pressure to 60 bar.

The process of the invention enables turnover numbers for the catalysts of the order of 100 000 and more for bromoaromatics as starting materials and 10 000 and more for chloroaromatics to be achieved. These values correspond to the best known results which have been achieved using phosphine ligands.

Owing to the catalyst activities and stabilities, the process of the invention makes it possible for the first time to use extremely small amounts of catalyst so that the catalyst costs are not cost-limiting, in contrast to the known Suzuki reactions for the corresponding process.

In the process of the invention, catalyst contents of from 1 to 2 mol % are used in exceptional cases; they are usually <1 mol %, particularly preferably <0.2 mol %. Furthermore, phosphite ligands can be prepared more simply and inexpensively than the phosphine ligands used hitherto and they are easier to modify and more stable to oxidation reactions.

The biaryls prepared according to the invention are used, inter alia, in industry as intermediates for pharmaceuticals (ATII antagonists) and agrochemicals, as ligand precursors for metallocene catalysts, as optical brighteners and as building blocks for polymers.

The following examples illustrate the process of the invention without restricting it thereto.

EXAMPLES

General Procedure

In a pressure tube (from Aldrich), 8.2 mmol of aryl halide, 9 mmol of phenylboronic acid, 10 mmol of base, an appropriate amount of cocatalyst if used and also an appropriate amount of phosphite and palladium(II) acetate and 500 mg of diethylene glycol di-n-butyl ether (as internal standard for GC analysis) are added under an argon atmosphere to 8 ml of dry toluene. The tube is subsequently closed and placed in a silicone oil bath at 120° C. (or 140° C. in experiment No. 20). After a period of 20 hours, the tube is cooled to room temperature. The solids are dissolved in 10 ml of $CH_2Cl_2$ and 10 ml of 1 n aqueous sodium hydroxide. The organic phase is analyzed by gas chromatography. The products are isolated by distillation, crystallization from methanol/acetone mixtures or by column chromatography (silica gel, hexane/ethyl acetate mixtures).

Table 1 below indicates the starting materials used and the yields and turnover numbers (TONs) achieved.

TABLE 1

Overview of the examples according to the invention

| No. | Halo-aromatic | Base | Cocat. (mol %) | Phosphite | Pd [mol %] | P/Pd | GC yield [%] | TON |
|---|---|---|---|---|---|---|---|---|
| 1 | 4-Chloro-benzotrifluoride | $Na_2CO_3$ | — | $P(O^iPr)_3$ | 1 | 50 | 52 | 52 |
| 2 | 4-Chloro-benzotrifluoride | $Na_2CO_3$ | CsF (10) | $P(O^iPr)_3$ | 1 | 50 | 58 | 58 |
| 3 | 4-Chloro-benzotrifluoride | $Na_2CO_3$ | $CaF_2$ (10) | $P(O^iPr)_3$ | 1 | 50 | 69 | 69 |
| 4 | 4-Chloro-benzotrifluoride | $Na_2CO_3$ | $H_2O$ (50) | $P(O^iPr)_3$ | 1 | 50 | 70 | 70 |
| 5 | 4-Chloro-benzotrifluoride | $K_3PO_4$ | — | $P(O^iPr)_3$ | 1 | 50 | 61 | 61 |
| 6 | 4-Chloro-benzotrifluoride | $K_3PO_4$ | — | $P(O^iPr)_3$ | 0.001 | 50 | 15 | 15000 |
| 7 | 4-Chloro-benzotrifluoride | NaOH | — | $P(O^iPr)_3$ | 1 | 50 | 71 | 71 |
| 8 | 4-Chloro-benzotrifluoride | $Na_2CO_3$ | $H_2O$ (50) | $P(O-2,4-{}^tBu_2C_6H_3)_3$ | 1 | 10 | 70 | 70 |
| 9 | 4-Chloro-benzotrifluoride | $Na_2CO_3$ | $H_2O$ (50) | $P(Oet)_3$ | 1 | 50 | 43 | 43 |
| 10 | 3-Chloro-benzotrifluoride | $Na_2CO_3$ | — | $P(O^iPr)_3$ | 1 | 50 | 52 | 52 |
| 11 | 4-Chloro-nitro-benzene | $Na_2CO_3$ | — | $P(O-2,4-{}^tBu_2C_6H_3)_3$ | 0.1 | 10 | 57 | 570 |
| 12 | 4-Chloro-acetophenone | $Na_2CO_3$ | — | $P(O-2,4-{}^tBu_2C_6H_3)_3$ | 0.1 | 10 | 53 | 530 |
| 13 | 2-Chloro-benzonitrile | $Na_2CO_3$ | — | $P(O^iPr)_3$ | 1 | 10 | 80 | 80 |
| 14 | 4-Bromo-fluorobenzene | $Na_2CO_3$ | — | $P(O-2,4-{}^tBu_2C_6H_3)_3$ | 0.1 | 10 | 72 | 720 |
| 15 | 4-Bromo-fluorobenzene | $Na_2CO_3$ | — | $P(O-2,4-{}^tBu_2C_6H_3)_3$ | 0.0001 | 10 | 24 | 240000 |
| 16 | 4-Bromo-toluene | $Na_2CO_3$ | — | $P(O-2,4-{}^tBu_2C_6H_3)_3$ | 0.1 | 10 | 86 | 860 |
| 17 | Bromo-benzene | $Na_2CO_3$ | — | $P(O-2,4-{}^tBu_2C_6H_3)_3$ | 0.1 | 10 | 87 | 870 |
| 18 | 2-Bromo-6-methoxy-naphthalene | $Na_2CO_3$ | — | $P(O-2,4-{}^tBu_2C_6H_3)_3$ | 0.1 | 10 | 69 | 690 |

TABLE 1-continued

Overview of the examples according to the invention

| No. | Halo-aromatic | Base | Cocat. (mol %) | Phosphite | Pd [mol %] | P/Pd | GC yield [%] | TON |
|---|---|---|---|---|---|---|---|---|
| 19 | Chlorobenzene | NaOH | — | P(O-2,4-$^tBu_2C_6H_3)_3$ | 1 | 10 | 54 | 54 |
| 20 | 4-Chlorotoluene | NaOH | — | P(O-2,4-$^tBu_2C_6H_3)_3$ | 1 | 10 | 45 | 45 |
| 21 | 2-Bromo-6-methoxynaphthalene | NaOH | — | P(O$^i$Pr)$_3$ | 0.0001 | 100 | 82 | 820000 |
| 22 | 4-Bromofluorobenzene | NaOH | — | P(O-2,4-$^tBu_2C_6H_3)_3$ | 0.0001 | 100 | 66 | 660000 |
| 23 | Bromobenzene | NaOH | — | P(O-2,4-$^tBu_2C_6H_3)_3$ | 0.0001 | 100 | 85 | 850000 |
| 24 | 4-Bromotoluene | NaOH | — | P(O-2,4-$^tBu_2C_6H_3)_3$ | 0.0001 | 100 | 69 | 690000 |

The examples demonstrate that the process of the invention makes it possible to achieve yields of at least 43% and in many cases more than 70% at increased turnover numbers or to achieve very high turnover numbers at certain yields.

What is claimed is:

1. A process for preparing monofunctional, bifunctional and/or polyfunctional biaryls of the formula (I)

$$Ar-Ar' \quad (I)$$

where Ar and Ar' are each, independently of one another,
an aromatic radical having up to 14 carbon atoms or
a heteroaromatic selected from the group consisting of five-, six- or seven-membered rings having at least one nitrogen, oxygen and/or sulfur atom in the ring;

by reacting haloaromatics of the formula (II)

$$Ar-X \quad (II)$$

with boron compounds of the formula (IIIa), (IIIb) and/or (IIIc)

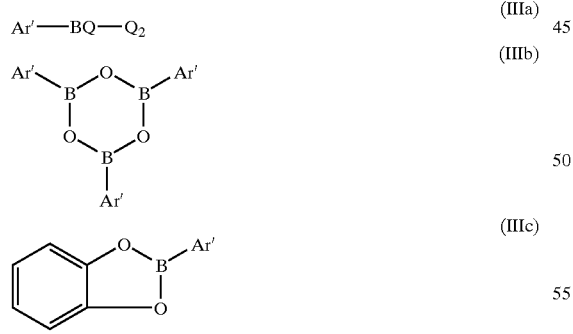

where, in the formulae (II), (IIIa), (IIIb) and (IIIc),
Ar and Ar' are as defined for formula (I);
X is selected from the group consisting of chlorine, bromine, iodine, $OSO_2CF_3$, $OSO_2$aryl-$(C_6-C_{10})$, $OSO_2$alkyl-$(C_1-C_8)$ and $N_2^+Y^-$, where Y is a chlorine, bromine or iodine atom or a tetrafluoroborate or tetraphenylborate anion;
$Q_1$ and $Q_2$ are selected independently from the group consisting of OH, fluorine, chlorine, bromine, iodine, alkyl-$(C_1-C_4)$, aryl-$(C_6-C_{10})$, alkoxy-$(C_1-C_4)$ and aryloxy-$(C_6-C_{10})$;

in the presence of at least one palladium complex of the formula (IVa) or (IVb),

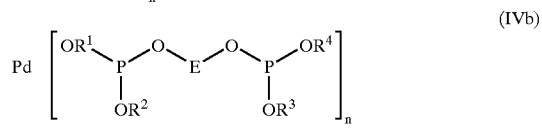

where
the radicals $R^1$ to $R^4$ are each, independently of one another, a $(C_1-C_{18})$-alkyl radical or one of the above-described radicals Ar;
E is a carbon bridge having from two to seven carbon atoms; and
n and m are each, independently of one another, an integer from 1 to 4,
and where the palladium complexes of the formula (IVa) or (IVb) are obtained in situ from at least one palladium(II) salt or a palladium(0) compound and a corresponding phosphite ligand and the molar ratio of the palladium(0) compound used or the palladium(II) salt to phosphite ligand used is in the range from 1:5 to 1:200.

2. The process as claimed in claim 1, wherein
the aromatic radicals Ar and Ar' have up to eight substituents;
the heteroaromatic has up to five substituents; and
the radicals $R^1$ to $R^4$ have up to eight substituents,
said substituents selected independently from the group consisting of fluorine, chlorine, $CF_3$, OH, $NO_2$, CN, $R^5$, O—$R^5$, CHO, CO—$R^5$, COOH, COO—$R^5$, OCO—$R^5$, $SiR^5_3$, $NH_2$, NH—$R^5$, N—$R^5_2$, SO—$R^5$, $SO_2$—$R^5$, $SO_3H$, $SO_3$—$R^5$, $COHN_2$, NHCOH, NHCO—$R^5$, NHCOO—$R^5$, CHCH—$CO_2$-alkyl-$(C_1-C_8)$, PO—$R^5_2$, P—$R^5_2$, $PO_3H_2$, PO(O-alkyl-$(C_1-C_6))_2$ and $CHCHCO_2H$;
where $R^5$ is an alkyl radical having from 1 to 8 carbon atoms or an aryl radical having from 6 to 10 carbon atoms.

3. The process as claimed in claim 1, wherein the carbon bridge E has up to seven substituents selected independently from the group consisting of $(C_1-C_4)$-alkyl, O-alkyl $(C_1-C_4)$, OH and Ar, where Ar is as defined for formula (I).

4. The process as claimed in claim 1, wherein $Q_1$ and $Q_2$ in the formula (IIIa) are each, independently of one another, a $(C_1-C_4)$-alkyl, $(C_1-C_4)$-alkoxy, $(C_6-C_{10})$-aryl or $(C_6-C_{10})$-aryloxy radical which is substituted by at least one halogen atom or a $(C_1-C_4)$-alkoxy or $(C_1-C_4)$-alkyl radical.

5. The process as claimed in claim 1, wherein $Q_1$ and $Q_2$ in the formula (IIIa) are together an alkylenedioxy or alkylene group which has from one to four carbon atoms and may be substituted by up to four $(C_1-C_4)$-alkyl and $(C_6-C_{10})$-aryl radicals.

6. The process as claimed in claim 1, wherein the radicals Ar and Ar' are each, independently of one another, a heteroaromatic in which up to four further aromatic, heteroaromatic and aliphatic rings are fused onto the heteroaromatic ring.

7. The process as claimed in claim 1, wherein the radicals Ar and Ar' are each, independently of one another, a substituted phenyl, naphthyl, anthryl, phenanthryl, biphenyl, pyridine, pyrimidine, oxazole, imidazole, pyrazine, quinoline, indole, furan, benzofuran or thiophene radical.

8. The process as claimed in claim 1, wherein the radicals Ar and Ar' each have, independently of one another, up to 5 substituents selected from the group consisting of alkyl-$(C_1-C_8)$, O-alkyl-$(C_1-C_8)$, OCO-alkyl-$(C_1-C_8)$, N-alkyl$_2$-$(C_1-C_8)$, phenyl, aryl, fluorine, chlorine, $NO_2$, CN, COOH, CHO, $SO_2$-alkyl-$(C_1-C_4)$, NH-alkyl-$(C_1-C_9)$, COO-alkyl-$(C_1-C_8)$, $CONH_2$, CONH-alkyl-$(C_1-C_8)$, CO-alkyl-$(C_1-C_8)$, CO-phenyl and P(O-phenyl)$_2$.

9. The process as claimed in claim 1, wherein the reaction is carried out in the presence of at least one solvent selected from the group consisting of water, aliphatic ethers, aromatic hydrocarbons, aliphatic hydrocarbons, alcohols, esters, aromatic nitriles, aliphatic nitriles and dipolar aprotic solvents.

10. The process as claimed in claim 9, wherein the solvent is THF, dioxane, diethyl ether, diglyme, MTBE, DME, acetonitrile, toluene, xylene, anisole, ethyl acetate, methanol, ethanol, butanol, ethylene glycol, ethylene carbonate, propylene carbonate, dimethyl sulfoxide, N,N-dimethylacetamide, N,N-dimethylformamide or N-methylpyrrolidone.

11. The process as claimed in claim 1, wherein the reaction is carried out in the presence of at least one base selected from the group consisting of primary amines, secondary amines, tertiary amines, alkali metal salts of aliphatic carboxylic acids, alkali metal salts of aromatic carboxylic acids, alkaline earth metal salts of aliphatic carboxylic acids and alkaline earth metal salts of aromatic carboxylic acids.

12. The process as claimed in claim 11, wherein the base is a carbonate, hydroxide or phosphate of lithium, sodium, potassium, calcium, magnesium or cesium.

13. The process as claimed in claim 1, wherein the reaction is carried out in the presence of at least one fluoride salt.

14. The process as claimed in claim 1, wherein the palladium(0) compound is selected from the group consisting of palladium(0)-dibenzylideneacetone complexes, tetrakis(triphenyl phosphite)palladium(0), tetrakis(triethylphosphite)-palladium(0), tetrakis(triphenylphosphine)palladium(0), bis(tri-o-tolylphosphine)-palladium(0), tricyclohexylphosphinepalladium(0) diallyl ether complex and bis(tricyclohexylphosphine)-palladium(0).

15. The process as claimed in claim 1, wherein the palladium (II) salt is selected from the group consisting of palladium(II) acetate, palladium(II) chloride, palladium(II) bromide, lithium tetrachloropalladate(II), palladium(II) acetylacetonate, palladium(II)propionate, bis-(acetonitrile) palladium(II) chloride, bis(tri-phenylphosphine)palladium (II) dichloride and bis(benzonitrile)palladium(II) chloride.

16. The process as claimed in claim 1, wherein the reaction is carried out in the presence of at least one cocatalyst selected from the group consisting of halogen salts.

17. The process as claimed in claim 16, wherein the halogen salt is LiBr, LiCl, NaBr, KBr, CsBr, Bu$_4$NCl, Bu$_4$NBr, benzyltrimethylammonium bromide, trioctylmethylammonium bromide or tetraphenylphosphonium bromide.

18. The process as claimed in claim 16, wherein the cocatalyst is present in an amount of from 0.001 mol % to 100 mol %, based on the compound of the formula (II).

19. The process as claimed in claim 16, wherein the reaction is carried out in the presence of the molten cocatalyst (salt melt).

20. The process as claimed in claim 1, wherein the reaction is carried out at a temperature of from 20 to 200° C.

21. The process as claimed in claim 1, wherein the reaction is carried out at a pressure of up to 100 bar.

22. The process as claimed in claim 1, wherein the aryl radial is phenyl.

23. The process as claimed in claim 9, wherein the polar aprotic solvent is selected from the group consisting of dialkyl sulfoxides, N,N-dialkylamides of aliphatic carboxylic acids and alkylated lactams.

24. The process as claimed in claim 11, wherein the amine is an alicyclic or open chain amine selected from the group consisting of alkylamines, dialkylamines and trialkylamines.

25. The process as claimed in claim 11, wherein the metal salt of a carboxylic acid is selected from the group consisting of acetates, propionates and benzoates.

26. The process as claimed in claim 25, wherein the metal salt is a carbonate, hydrogen carbonate, phosphate, hydrogen phosphate and hydroxide.

27. The process as claimed in claim 11, wherein the metal alkoxide is an alkali metal alkoxide or alkaline earth metal alkoxide.

28. The process as claimed in claim 27, wherein the metal alkoxide is selected from the group consisting of sodium methoxide, potassium methoxide, sodium ethoxide, magnesium methoxide and calcium ethoxide.

29. The process as claimed in claim 13, wherein the fluoride salt is selected from the group consisting of CaF$_2$, NaF, KF, LiF, CsF and $((C_1-C_8)\text{alkyl})_4\text{NF}$.

30. The process as claimed in claim 16, wherein the halogen salt is selected from the group consisting of alkali metals, alkaline earth metals, ammonium halide, phosphonium halide and mixtures thereof.

31. The process as claimed in claim 30, wherein the halogen salt is a bromide or chloride.

32. The process as claimed in claim 18, wherein the cocatalyst is present in an amount from 0.01 to 50 mol %.

33. The process as claimed in claim 20, wherein the reaction is carried out at a temperature of from 60 to 180° C.

34. The process as claimed in claim 20, wherein the reaction is carried out at a temperature of from 80 to 160° C.

35. The process as claimed in claim 21, wherein the reaction is carried out at a pressure of from atmospheric pressure to 60 bar.

* * * * *